United States Patent
Ding et al.

(10) Patent No.: US 11,335,040 B2
(45) Date of Patent: May 17, 2022

(54) MULTI-FOCAL NON-PARALLEL COLLIMATOR-BASED IMAGING

(71) Applicant: Siemens Medical Solutions USA, Inc., Malvern, PA (US)

(72) Inventors: Xinhong Ding, Buffalo Grove, IL (US); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 298 days.

(21) Appl. No.: 16/649,681

(22) PCT Filed: Aug. 28, 2018

(86) PCT No.: PCT/US2018/048218
§ 371 (c)(1),
(2) Date: Mar. 23, 2020

(87) PCT Pub. No.: WO2019/112658
PCT Pub. Date: Jun. 13, 2019

(65) Prior Publication Data
US 2020/0258272 A1    Aug. 13, 2020

Related U.S. Application Data

(60) Provisional application No. 62/594,752, filed on Dec. 5, 2017.

(51) Int. Cl.
*G06T 11/00* (2006.01)
*G06N 3/04* (2006.01)
(Continued)

(52) U.S. Cl.
CPC .............. *G06T 11/008* (2013.01); *G06N 3/04* (2013.01); *G06N 3/08* (2013.01); *A61B 6/032* (2013.01);
(Continued)

(58) Field of Classification Search
CPC ... G06T 7/0012; G06T 11/003; G06T 11/008; G06T 2207/10104; G06T 2207/10108;
(Continued)

(56) References Cited

U.S. PATENT DOCUMENTS

| 6,950,494 B2 | 9/2005 | Vija et al. |
| 7,737,406 B2 | 6/2010 | Vija et al. |

(Continued)

OTHER PUBLICATIONS

"Deep learning based attenuation correction for the Time-of-Flight position emission tomography"; I.P. Com, I.P. Com Inc., West Henrietta, NY, US; Jan. 20, 2017 (Jan. 27, 2017); XP013174148; ISSN: 1533-0001.

(Continued)

*Primary Examiner* — Andrew W Johns

(57) ABSTRACT

A system and method include training of an artificial neural network to generate a simulated attenuation-corrected reconstructed volume from an input non-attenuation-corrected reconstructed volume, the training based on a plurality of non-attenuation-corrected volumes generated from respective ones of a plurality of sets of two-dimensional emission data and on a plurality of attenuation-corrected reconstructed volumes generated from respective ones of the plurality of sets of two-dimensional emission data.

20 Claims, 8 Drawing Sheets

(51) Int. Cl.
    *G06N 3/08*    (2006.01)
    *A61B 6/03*    (2006.01)
    *A61B 6/06*    (2006.01)

(52) U.S. Cl.
    CPC .............. *A61B 6/037* (2013.01); *A61B 6/06* (2013.01); *G06T 2210/41* (2013.01)

(58) Field of Classification Search
    CPC . G06T 2207/20081; G06T 2207/20084; G06T 2210/41; A61B 6/037; A61B 6/5258; A61B 2576/00; G06N 3/08; G06N 20/00
    See application file for complete search history.

(56) References Cited

U.S. PATENT DOCUMENTS

| | | | |
|---|---|---|---|
| 10,593,071 B2* | 3/2020 | Ding et al. | G06T 7/0012 |
| 2009/0110256 A1* | 4/2009 | Thielemans et al. | A61B 6/037 382/131 |
| 2010/0010757 A1 | 1/2010 | Schmidt | 702/57 |
| 2013/0034286 A1 | 2/2013 | Vija et al. | |
| 2015/0117733 A1* | 4/2015 | Manjeshwar et al. | G06T 11/003 382/131 |
| 2016/0163095 A1 | 6/2016 | Wollenweber | |
| 2017/0011185 A1 | 1/2017 | Schweizer | |
| 2017/0024634 A1 | 1/2017 | Miao et al. | |

OTHER PUBLICATIONS

Glick, Stephen J. et al, "An Analytical Approach for Compensation of Non-Unifrom Attenuation in Cardiac SPECT imaging", Physics in Medicine & Biology 40, Jun. 13, 1995, (pp. 1677-1693), 17 pp.

Wallis, Jerold W. et al., "Attenuation Correction in Cardiac SPECT without a Transmission Measurement", Mallinckrodt Institute of Radiology, Washington University School of Medicine, Journal of Nuclear Medicine, 1995, (pp. 506-512), 8 pp.

Maksud, Philippe et al., "Artificial Nueral Network as a Tool to Compensate for Scatter and Attenuation in Radionuclide Imaging", Journal of Nuclear Medicine, 1996, (pp. 735-745), 12 pp.

Kaplan, M.S. et al., "A Differential Attenuation Method for Simultaneous Estimation of SPECT Activity and Attenuation Distributions", IEEE, 1999, (pp. 1678-1683), 6 pp.

Kaplan, M.S et al., "Comparison of the Differential Attenuation Method for Multi-Emission SPECT with Conventional Methods of Attenuation Compensation", IEEE, 2000, (pp. 879-883), 5 pp.

Zaidi, Habid et al., "Determination of the Attenuation Map in Emission Tomography", Journal of Nuclear Medicine, 2003, (pp. 291-315), 25 pp.

Du, Yong et al., "Model-based compensation for quantitative 123 I brain SPECT imaging", Physics in Medicine & Biology 51, Feb. 15, 2006, (pp. 1269-1282), 14 pp.

Cade, Sarah C. et al. "Use of measured scatter data for the attenuation correction of single photon emission tomography without transmission scanning", Medical Physics 40, Jul. 2013, (p. 082506-1 through 082506-12) 12 pp.

Nogueira, et al., "An arlificial neural networks approach for assessment treatment response in oncological patients using PET/CT images." BMC medical imaging. Feb. 13, 2017, retrieved from <https://bmcmedimaging.biomedcentral.com/track/pdf.10.1186/s12880-017-0181-0>.

International Search Report for Corresponding PCT application No. PCT/US2018/048218, dated Nov. 5, 2018.

* cited by examiner

MULTI-FOCAL NON-PARALLEL COLLIMATOR-BASED IMAGING

CROSS-REFERENCE TO RELATED APPLICATIONS

The present application is related to and claims priority to U.S. Provisional Patent Application No. 62/594,752, filed Dec. 5, 2017, the contents of which are incorporated by reference in their entirety, for all purposes.

BACKGROUND

Conventional medical images may be generated via transmission imaging or emission imaging. In transmission imaging, the imaging source (e.g., an X-ray source) is external to the subject and the source radiation (e.g., X-rays) is transmitted through the subject to a detector. According to emission imaging, the imaging source (e.g., a gamma ray-emitting radiopharmaceutical) is internal to the subject (e.g., due to injection or ingestion thereof) and the source radiation (e.g., gamma rays) is emitted from within the subject to a detector. In either case, absorption or scattering within the subject tissue attenuates the source radiation prior to reception of the source radiation by the detector.

Images are generated by determining the distribution of this attenuation over three-dimensional space. Determining the attenuation is relatively straightforward in the case of transmission imaging, since the amount of the external source radiation being transmitted through the subject and the amount received at the detector are both known. However, the determination of attenuation in emission imaging is more difficult, because the amount of radiation being emitted by the emission source(s) within the subject cannot be measured directly.

Accordingly, in emission imaging such as single-photon-emission-computer-tomography (SPECT) and positron-emission-tomography (PET), attenuation corrections are employed during image generation in order to improve image quality. These attenuation corrections may be particularly helpful for imaging systems which use multi-focal non-parallel collimators. Specifically, due to the strongly location-dependent point spread function (PSF) responses of these collimators, images generated without attenuation corrections may be difficult for a radiologist to properly interpret.

Attenuation corrections are typically based on Linear Attenuation Coefficient (LAC) maps ("mu-maps") derived from a Computed Tomography (CT) scan of the subject tissue. Such a CT scan is typically performed during the same imaging session at which the emission imaging is performed. For example, emission data of a portion of a patient may be acquired while the patient is positioned in an imaging position, and CT data of a similar portion of the patient may be acquired by a CT scan while the patient remains substantially in the imaging position. A transform is applied to the CT data to generate a mu-map of the portion of the patient. Lastly, an image reconstruction process generates an attenuation-corrected volume based on the emission data and the mu-map.

The CT scan required to generate the mu-map delivers an undesirable radiation dose to the subject tissue. Also, some imaging systems lack the ability to perform emission imaging and a contemporaneous CT scan. What is needed are efficient systems to generate improved reconstructed images without requiring a CT scan.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide generation of a simulated attenuation-corrected volume from an input non-attenuation-corrected reconstructed volume. For example, an artificial neural network may be trained to generate a simulated attenuation-corrected volume based on a plurality of non-attenuation-corrected reconstructed volumes and on CT attenuation-corrected reconstructed volumes generated based on the same two-dimensional emission data.

According to some embodiments, the trained network implements a particular function of the inputs to the network. The function may be exported to another system to receive a non-attenuation-corrected reconstructed volume (or emission data from which a non-attenuation-corrected reconstructed volume may be generated) and generate a simulated attenuation-corrected volume based thereon. In one example, the training generates parameter values for kernels of a fully convolutional network. Another fully convolutional network comprising thusly-parameterized kernels may be efficiently incorporated within a SPECT or PET reconstruction algorithm to generate a simulated attenuation-corrected volume based on emission data.

Some embodiments provide technical improvements over existing systems which require a separate CT scan and its resultant additional radiation dose, and/or which produce unsatisfactory reconstructed images from emission data. One such technical improvement is the ability to generate medical images of greater clinical accuracy and/or to subject a patient to less radiation exposure than existing imaging systems.

Figure 1:
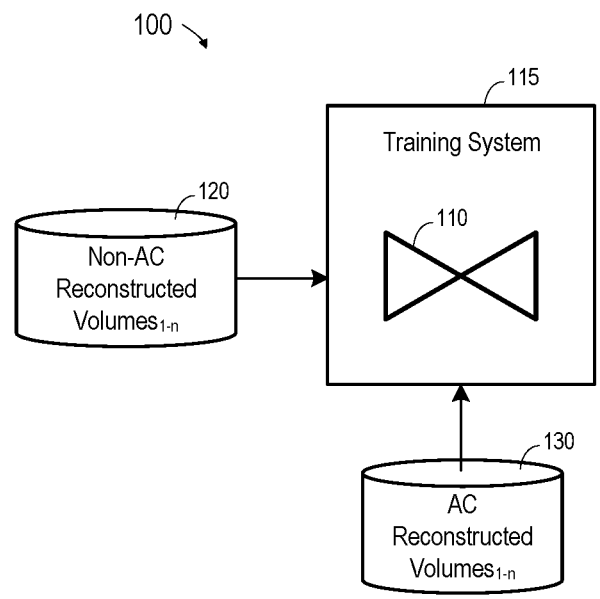
FIG. 1 is a block diagram of a system to train an artificial neural network to generate a simulated attenuation-corrected image according to some embodiments.

FIG. 1 illustrates system 100 to train an artificial neural network to generate a simulated attenuation-corrected volume according to some embodiments. Training system 115 uses non-attenuation-corrected reconstructed volumes$_{1-n}$ 120 and attenuation-corrected reconstructed volumes$_{1-n}$ 130 to train artificial neural network 110. According to some embodiments, non-attenuation-corrected reconstructed volumes$_{1-n}$ 120 may comprise SPECT image volumes reconstructed based on emission data acquired using a multi-focal non-parallel collimator, and attenuation-corrected reconstructed volumes$_{1-n}$ 130 may comprise volumes reconstructed based on the same emission data and on CT data (or other transmission data). The CT data provides information for such that reconstructed volumes$_{1-n}$ 130 may be considered attenuation-corrected. As described above, an attenuation-corrected volume may be more-easily or accurately interpreted than its non-attenuation-corrected counterpart.

Non-attenuation-corrected reconstructed volumes$_{1-n}$ 120 may comprise SPECT image volumes reconstructed based on emission data acquired using a parallel hole collimator. A parallel hole collimator may be viewed as a multi-focal collimator in which the focal lengths approach infinity.

Attenuation-corrected reconstructed volumes$_{1-n}$ 130 represent ground truth data for evaluating the performance of network 110 during training by training system 115. For example, for each x=1 through n, training system 115 may input a non-attenuation-corrected reconstructed volume$_x$ 120 to network 110 and compare the resulting output against attenuation-corrected reconstructed volume$_x$ 130. Network 110 is then modified based on the comparisons and the process repeats until satisfactory performance is achieved.

Artificial neural network 110 may comprise any type of network which is trainable to approximate a function. In some embodiments, network 110 receives a three-dimensional image and outputs a three-dimensional image. Network 110 may comprise an implementation of a "u-net" convolutional network architecture as is known in the art.

Generally, artificial neural network 110 may comprise a network of neurons which receive input, change internal state according to that input, and produce output depending on the input and internal state. The output of certain neurons is connected to the input of other neurons to form a directed and weighted graph. The weights as well as the functions that compute the internal state can be modified by a training process based on ground truth data. Artificial neural network 110 may comprise any one or more types of artificial neural network that are or become known, including but not limited to convolutional neural networks, recurrent neural networks, long short-term memory networks, deep reservoir computing and deep echo state networks, deep belief networks, and deep stacking networks.

Training system 115 may comprise any system or systems for training an artificial neural network that are or become known. For example, training system 115 may employ supervised learning, unsupervised learning and/or reinforcement learning.

According to some embodiments, trained artificial neural network 110 implements a function. The function may be characterized as a set of parameter values associated with each network node. The function may be deployed as is known in the art to an external system such as system 200 of FIG. 2.

System 200 includes trained network 210. Network 210 may be trained as described above with respect to network 100. Although depicted as a neural network, network 210 may comprise any type of processing system to implement the function resulting from the training of network 110 of FIG. 1. For example, network 210 may comprise a software application programmed to implement a function generated via prior neural network training. System 200 may be operated temporally and/or geographically distant from the training depicted in FIG. 1. For example, system 100 may comprise a data processing facility while system 200 may comprise an imaging theater in which a patient has just been imaged.

In operation, non-attenuation-corrected reconstructed volume 220 is acquired and is input to trained network 210. The type or format of volume 220 corresponds to the type and format of the volumes used to train network 110. Network 210 then operates to output simulated attenuation-corrected reconstructed volume 230 based on the input volume 220. As described above, simulated attenuation-corrected reconstructed volume 230 may be more clinically accurate and/or useful than non-attenuation-corrected reconstructed volume 220, particularly in a case where non-attenuation-corrected reconstructed volume 220 is based on emission data acquired using a multi-focal non-parallel collimator. Moreover, simulated attenuation-corrected reconstructed volume 230 may be generated without exposing a patient to radiation in excess of the radiation used in the generation of volume 220.

Figure 3:
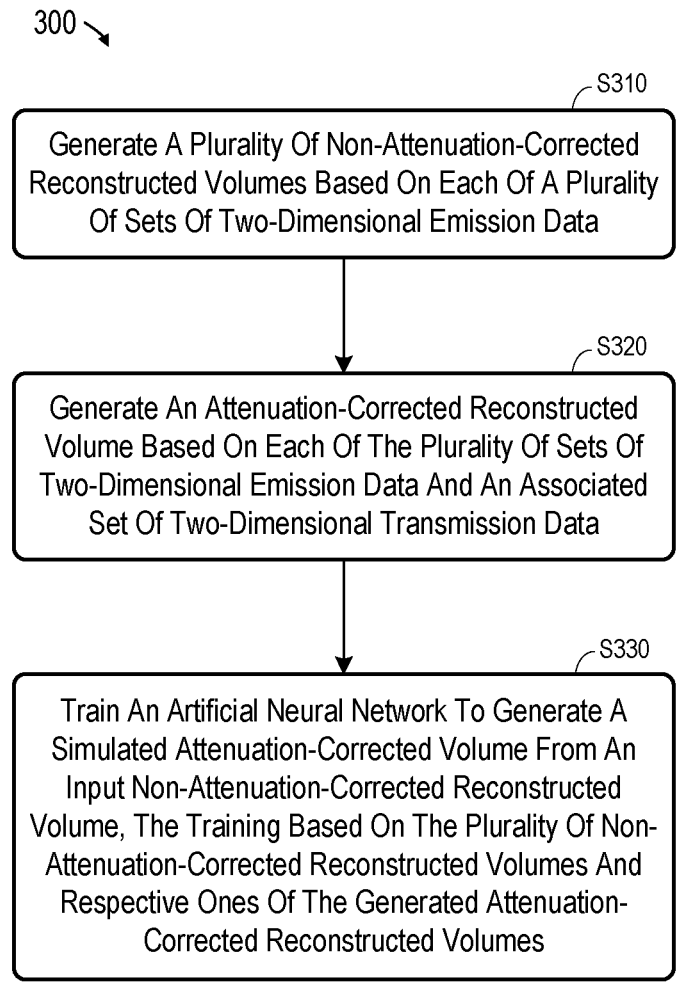
FIG. 3 is a flow diagram of a network training process according to some embodiments.

FIG. 3 is a flow diagram of a network training process according to some embodiments. Process 300 and the other processes described herein may be performed using any suitable combination of hardware and software. Software program code embodying these processes may be stored by any non-transitory tangible medium, including a fixed disk, a volatile or non-volatile random access memory, a floppy disk, a CD, a DVD, a Flash drive, or a magnetic tape. Embodiments are not limited to the examples described below.

Figure 4:
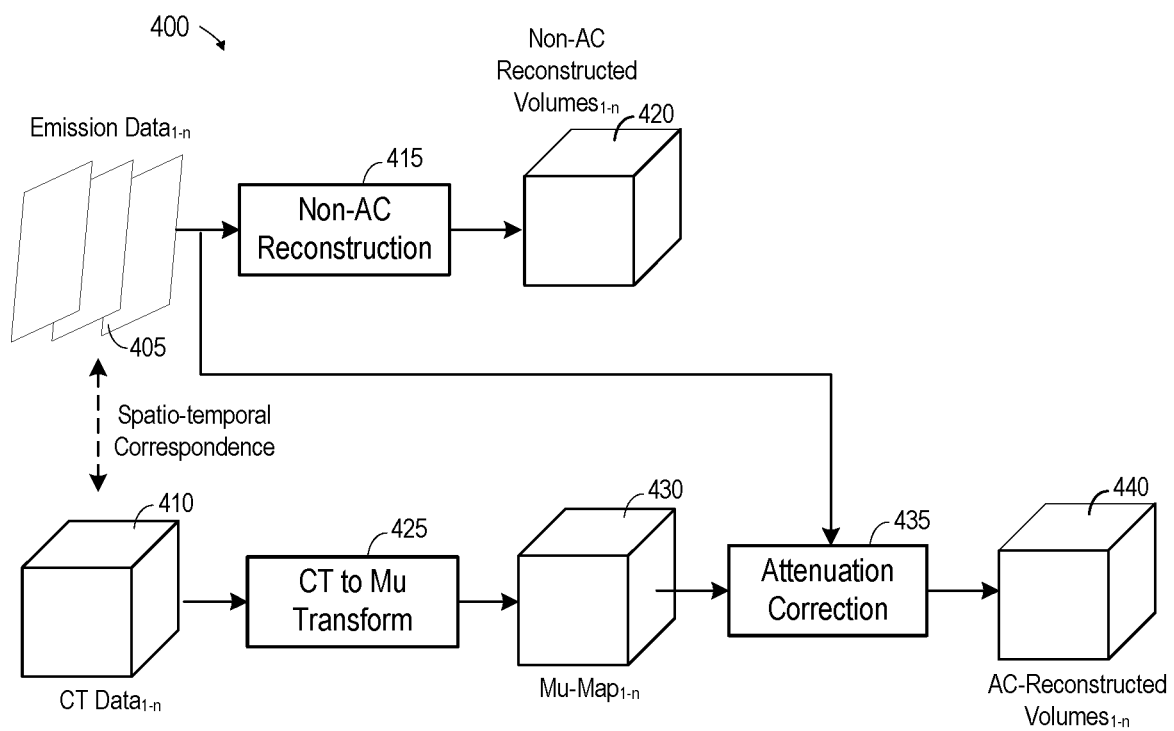
FIG. 4 is a block diagram illustrating acquisition of labeled training data according to some embodiments.

Initially, at S310, a plurality of non-attenuation-corrected volumes are generated. Each of the non-attenuation-corrected volumes may be generated based on respective sets of two-dimensional image data. FIG. 4 depicts system 400 to generate the non-attenuation-corrected volumes acquired at S310 according to some embodiments. For example, a first set of emission data (i.e., emission data$_1$) 405 is received by non-AC reconstruction component 415, which performs a reconstruction operation on emission data$_1$ 405 and outputs corresponding non-attenuation-corrected reconstructed volume$_1$ 420. This process repeats for a plurality of emission data$_{2-n}$, resulting in respective non-attenuation-corrected reconstructed volumes$_{2-n}$.

An attenuation-corrected reconstructed volume is generated based on each set of two-dimensional emission data and on an associated set of two-dimensional transmission data at S320. FIG. 4 depicts the generation of attenuation-corrected reconstructed volumes at S320 according to some embodiments. In the illustrated example, each of CT data$_{1-n}$ 410 was acquired by a CT scan executed substantially contemporaneous to the acquisition of a corresponding set of emission data$_{1-n}$. For example, a set of emission data 405 and corresponding CT data 410 may have been acquired by a SPECT/CT system as is known in the art.

CT to Mu transform component 425 applies a transform to each of CT data$_{1-n}$ to generate corresponding linear attenuation coefficient maps (mu-maps$_{1-n}$) 430. For example, a transform is applied to CT data$_1$ 410 to generate mu-map$_1$ 430, which in turn corresponds to emission data$_1$ 405. Next, attenuation correction component 435 generates an attenuation-corrected volume$_{1-n}$ 440 based on each corresponding set of emission data$_{1-n}$ 405 and its corresponding mu-map$_{1-n}$ 430.

According to some embodiments, generation of a mu-map based on CT data includes receiving output pixel data for a pixel of a CT image. The value of the pixel data is compared to a predetermined range. If the value is within the predetermined range, a linear attenuation coefficient is calculated from the pixel data using a first conversion function corresponding to the predetermined range. If the value is outside the predetermined range, the linear attenuation coefficient is calculated from the pixel data using a second conversion function corresponding to a range outside the predetermined range. The calculated coefficient is stored in a memory as part of a mu-map, and the process repeats for each other pixel of the CT image.

Generation of the volumes at S310 and/or S320 may comprise acquisition of the previously-generated volumes. One or more sets of emission data$_{1-n}$ 405 and corresponding CT data$_{1-n}$ 410 may be acquired by different imaging systems, which may differ from the system executing process 300. According to some embodiments, process 300 is performed by an Artificial Intelligence platform and the non-attenuation-corrected volumes and corresponding attenuation-corrected volumes are acquired from one or more data repositories.

An artificial neural network is trained at S330 to generate a simulated attenuation-corrected volume from an input non-attenuation-corrected reconstructed volume. The training is based on the plurality of non-attenuation-corrected volumes generated in S310 and respective ones of the attenuation-corrected volumes generated in S320. In some embodiments, training of the network involves determining a loss based on the output of the network and iteratively modifying the network based on the loss until the loss reaches an acceptable level or training otherwise terminates (e.g., due to time constraints or to the loss asymptotically approaching a lower bound).

Figure 5:
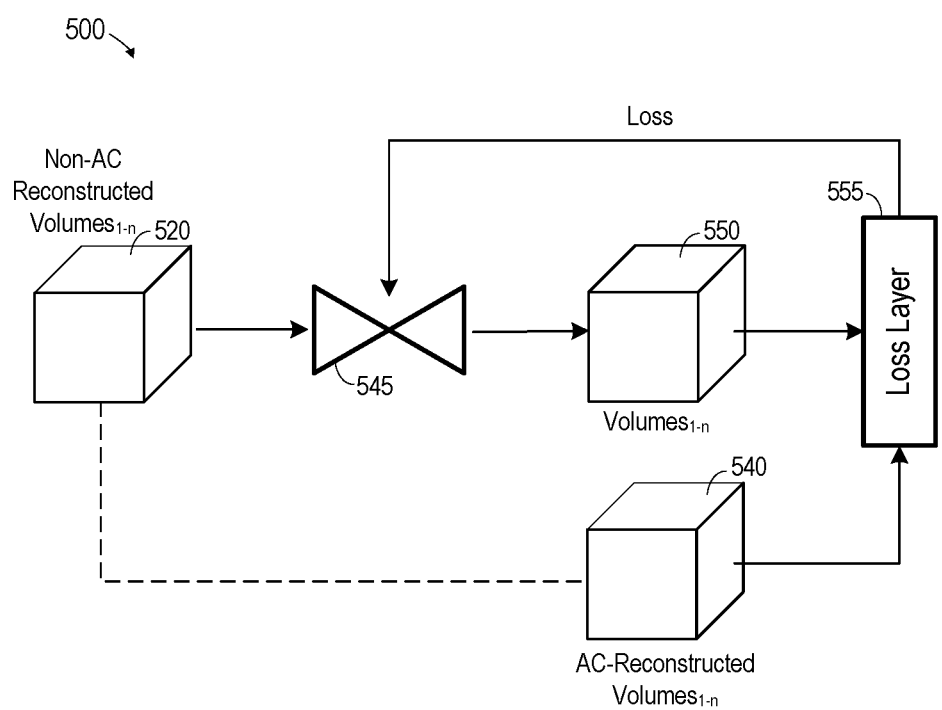
FIG. 5 is a block diagram of a system to train an artificial neural network to generate a simulated attenuation-corrected image according to some embodiments.

FIG. 5 illustrates training at S330 according to some embodiments. During training, network 545 receives non-attenuation-corrected reconstructed volumes$_{1-n}$ 520 acquired at S310 and generates a volume$_{1-n}$ 550 for each received volume$_{1-n}$ 520. Loss layer component 555 determines a loss by comparing each generated volume$_{1-n}$ 550 to a corresponding "ground truth" attenuation-corrected reconstructed volume$_{1-n}$ 540 acquired at S320. For example, and with reference to FIG. 4, network 545 generates volume$_{20}$ 550 based on non-attenuation-corrected volume$_{20}$ 550, which was reconstructed based on emission data$_{20}$ 405. Loss layer component 555 compares generated volume$_{20}$ 550 to attenuation-corrected volume$_{20}$ 540, which was generated based on CT data$_{20}$ 410 corresponding to emission data$_{20}$ 405.

The total loss is back-propagated from loss layer component 555 to network 545. The loss may comprise an L1 loss, and L2 loss, or any other suitable measure of total loss. An L1 loss is the sum of the absolute differences between each output volume and its corresponding ground truth volume, and an L2 loss is the sum of the squared differences between each output volume and its corresponding ground truth volume.

Figure 2:
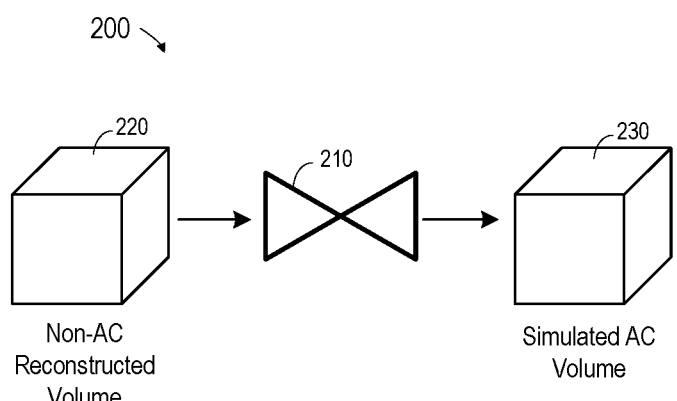
FIG. 2 is a block diagram of a system deploying a trained artificial neural network to generate a simulated attenuation-corrected image according to some embodiments.

Network 545 changes its internal weights, or kernel parameter values, based on the back-propagated loss as is known in the art. The training data is again processed by network 545 and loss layer 555 as described above, and the process repeats, until it is determined that the loss has reached an acceptable level or training otherwise terminates. At termination, network 545 may be considered trained. According to some embodiments, the function implemented by trained network 545 (e.g., embodied in parameter values of trained convolutional kernels) may then be deployed as shown in FIG. 2 in order to generate attenuation-corrected volumes based on non-attenuation-corrected volumes, and without requiring CT data-based attenuation correction.

Reconstruction component 415, transform component 425, attenuation correction component 435, and each functional component described herein may be implemented in computer hardware, in program code and/or in one or more computing systems executing such program code as is known in the art. Such a computing system may include one or more processing units which execute processor-executable program code stored in a memory system. Moreover, network 545 may comprise hardware and software specifically-intended for executing algorithms based on a specified network architecture and trained kernel parameters.

Figure 6:
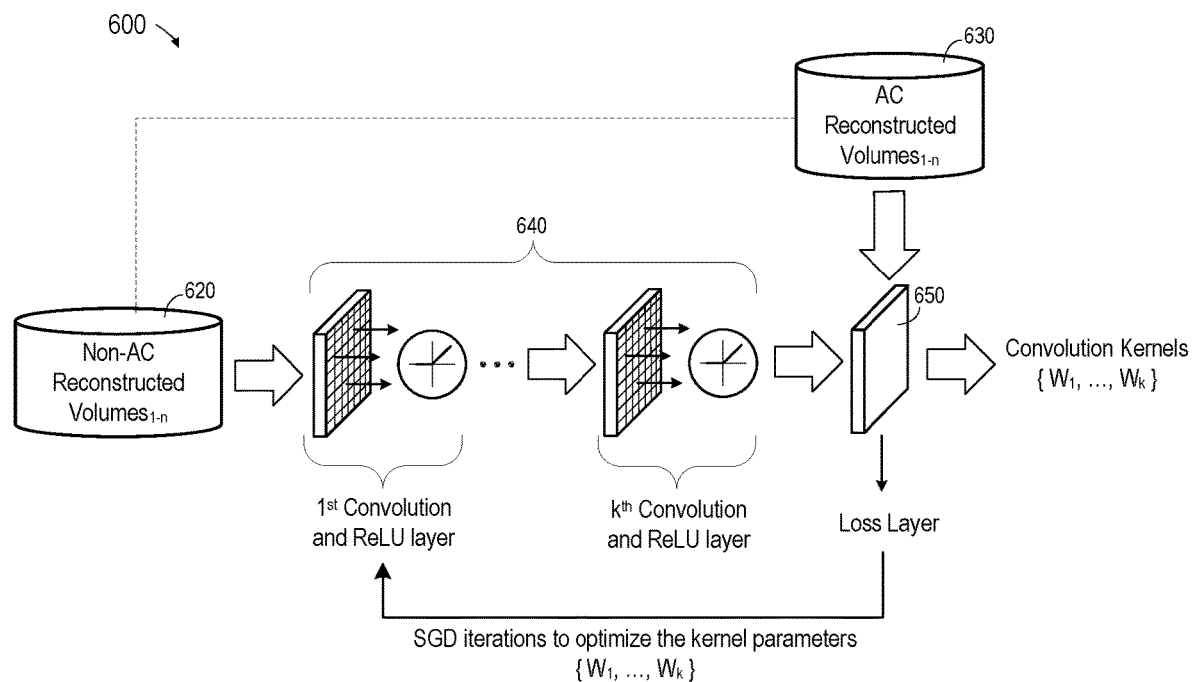
FIG. 6 is a detailed example of FIG. 5 in which a deep convolutional neural network is trained to generate a simulated attenuation-corrected image according to some embodiments.

FIG. 6 illustrates training architecture 600 according to some embodiments. Training architecture 600 may comprise an implementation of process 300 and/or system 500. For example, network 640 of architecture 600 may be trained based on a plurality of non-attenuation-corrected reconstructed volumes$_{1-n}$ 620 corresponding to a respective plurality of attenuation-corrected reconstructed volumes$_{1-n}$ 630.

Network 640 is a convolutional network consisting of k internal layers, where each internal layer is a convolution followed a rectified linear unit (ReLU) activate function. The convolution kernel parameters in a k-th layer are denoted by $W_k$. Loss layer 650 computes a measure of the difference between volumes output by network 640 and associated ones of attenuation-corrected reconstructed volumes$_{1-n}$ 630. The convolution kernels $\{W_1, \ldots, W_k\}$ are optimized based on the computed measures over several iterations, for example by using a stochastic gradient descent (SGD) algorithm. A network may then be deployed including the optimized kernel parameters, and fed a non-attenuation-corrected reconstructed volume in order to output a simulated attenuation-corrected reconstructed volume.

Figure 7:
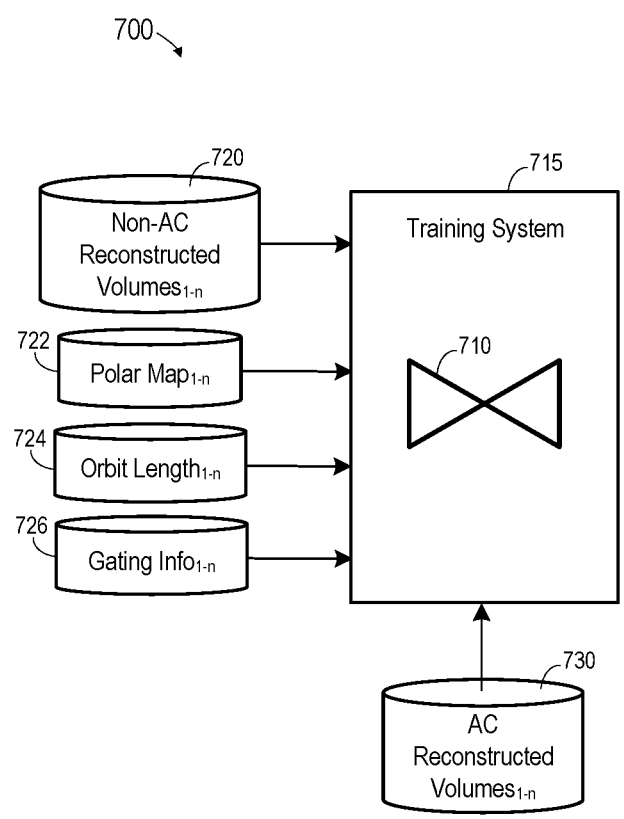
FIG. 7 is a block diagram of a system that uses additional information as inputs to train an artificial neural network to generate a simulated attenuation-corrected image according to some embodiments.

FIG. 7 illustrates architecture 700 including training data in addition to that depicted in FIG. 1. Specifically, training system 715 trains network 710 based on non-attenuation-corrected reconstructed volumes$_{1-n}$ 720 and on polar maps$_{1-n}$ 722, orbit lengths$_{1-n}$ 724 and gating information$_{1-n}$ 726. The use of additional network inputs may result in an increased accuracy (i.e., decreased loss) of network 710 after training. Embodiments may employ one or more of polar maps$_{1-n}$ 722, orbit lengths$_{1-n}$ 724 and gating information$_{1-n}$ 726.

According to one example, non-attenuation-corrected reconstructed volume$_x$ 720 is based on a set of emission data acquired during emission imaging. Polar map$_x$ 722 is generated based on the same set of emission data as is known in the art. Moreover, orbit length$_x$ 724 is an orbit length used to acquire the set of emission data and gating information$_x$ 726 indicates a gate (e.g., a point in the cardiac cycle) used to trigger acquisition of the set of emission data. The orbit may be isocenter-centric, cardio-centric or otherwise-positioned in some embodiments. This data may be input to network 710 and training system 715 may then compare the resulting output to ground truth attenuation-corrected reconstructed volume$_x$ 730 in order to train network 710.

Figure 8:
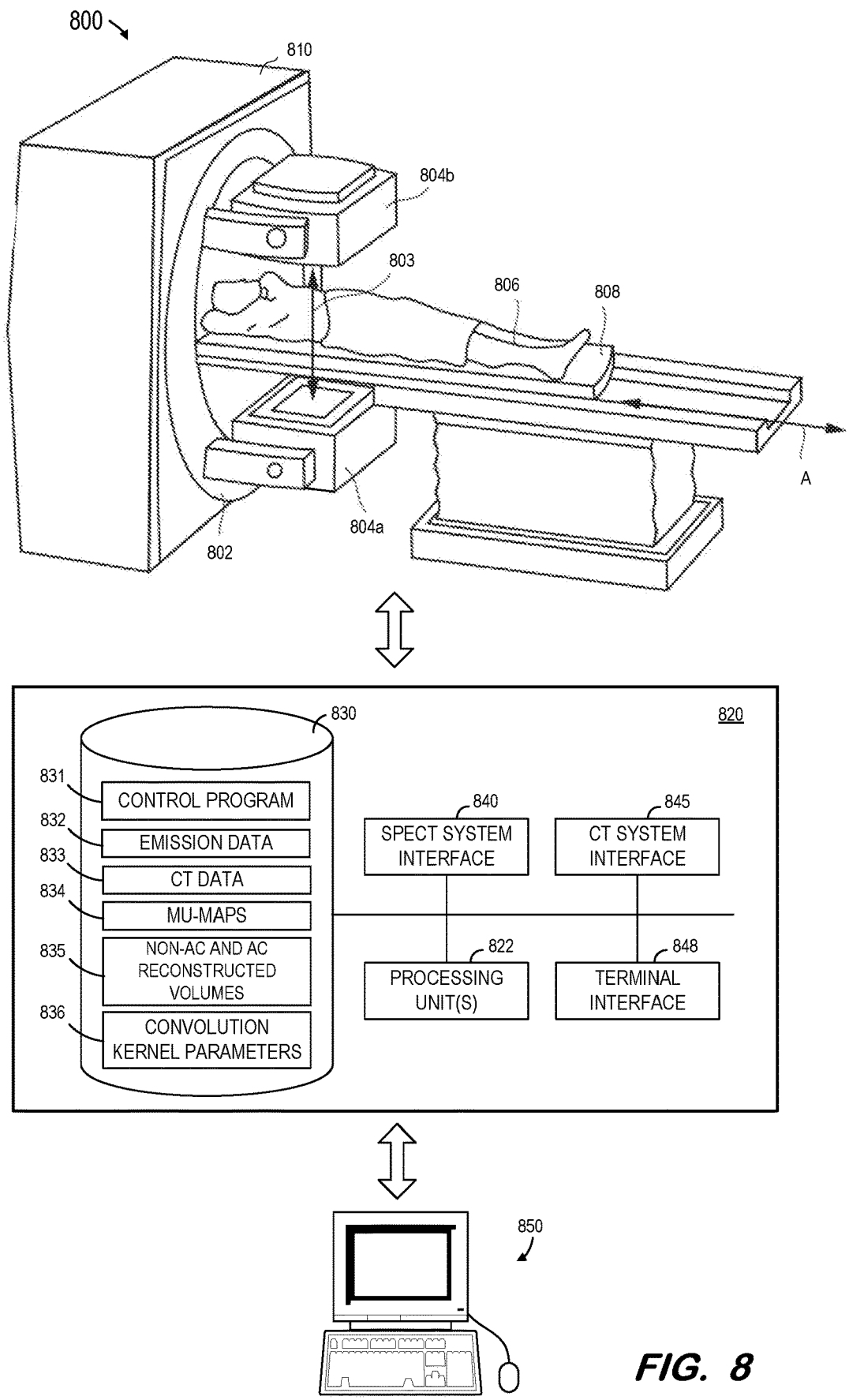
FIG. 8 illustrates a dual transmission and emission imaging SPECT/CT system according to some embodiments.

FIG. 8 illustrates SPECT-CT system 800 which may implement process 300 as described above. System 800 may further deploy a trained network to acquire emission data and generate attenuation-corrected volumes as described herein.

System 800 includes gantry 802 to which two or more gamma cameras 804a, 804b are attached, although any number of gamma cameras can be used. A detector within each gamma camera detects gamma photons (i.e., emission data) emitted by a radioisotope within the body of a patient 806 lying on a bed 808.

Bed 808 is slidable along axis-of-motion A. At respective bed positions (i.e., imaging positions), a portion of the body of patient 806 is positioned between gamma cameras 804a, 804b in order to capture emission data from that body portion. Gamma cameras 804a, 804b may include multi-focal cone-beam collimators or parallel-hole collimators as is known in the art.

System 800 also includes CT housing 810 including an X-ray imaging system (unshown) as is known in the art. Generally, and according to some embodiments, the X-ray imaging system acquires two-dimensional X-ray images of patient 806 before, during and/or after acquisition of emission data using gamma cameras 804a and 804b.

Control system 820 may comprise any general-purpose or dedicated computing system. Accordingly, control system 820 includes one or more processing units 822 configured to execute processor-executable program code to cause system 820 to operate as described herein, and storage device 830 for storing the program code. Storage device 830 may comprise one or more fixed disks, solid-state random access memory, and/or removable media (e.g., a thumb drive) mounted in a corresponding interface (e.g., a USB port).

Storage device 830 stores program code of system control program 831. One or more processing units 822 may execute system control program 831 to, in conjunction with SPECT system interface 840, control motors, servos, and encoders to cause gamma cameras 804a, 804b to rotate along gantry 802 and to acquire two-dimensional emission data at defined imaging positions during the rotation. The acquired data 832 may be stored in memory 830.

One or more processing units 822 may also execute system control program 831 to, in conjunction with CT system interface 845, cause a radiation source within CT housing 810 to emit radiation toward body 806 from different projection angles, to control a corresponding detector to acquire two-dimensional CT images, and to reconstruct three-dimensional CT images from the acquired images. The CT images may be acquired substantially contemporaneously with the emission data as described above, and the reconstructed images may be stored as CT data 833.

Control program 831 may be further executed to generate mu-maps 834 from CT data 833, and to reconstruct non-attenuation-corrected and attenuation-corrected reconstructed volumes 835 from emission data 832. Non-attenuation-corrected and attenuation-corrected reconstructed volumes 835 may then be used to train a network as described above. Convolution kernel parameters 836 may comprise the trained parameters of such a network.

After training of parameters 836, system 800 may be operated to acquire emission data and reconstruct a non-attenuation-corrected volume based on the emission data. The non-attenuation-corrected volume is then input to a network implementing trained parameters 836 to generate a simulated attenuation-corrected volume.

The simulated attenuation-corrected volume may be transmitted to terminal 850 via terminal interface 848. Terminal 850 may comprise a display device and an input device coupled to system 820. Terminal 850 may display any of two-dimensional emission data, CT data, mu-maps, etc., and may receive user input for controlling display of the data, operation of imaging system 800, and/or the processing described herein. In some embodiments, terminal 850 is a separate computing device such as, but not limited to, a desktop computer, a laptop computer, a tablet computer, and a smartphone.

According to some embodiments, a first system is used to acquire the emission data and the CT data, and to generate the non-attenuation-corrected and attenuation-corrected reconstructed volumes used to train a network, a second system is used to train the network, and the trained network is deployed by one or more other systems to generate simulated attenuation-corrected volumes without requiring CT data.

Each of component of system 800 may include other elements which are necessary for the operation thereof, as well as additional elements for providing functions other than those described herein.

Figure 9:
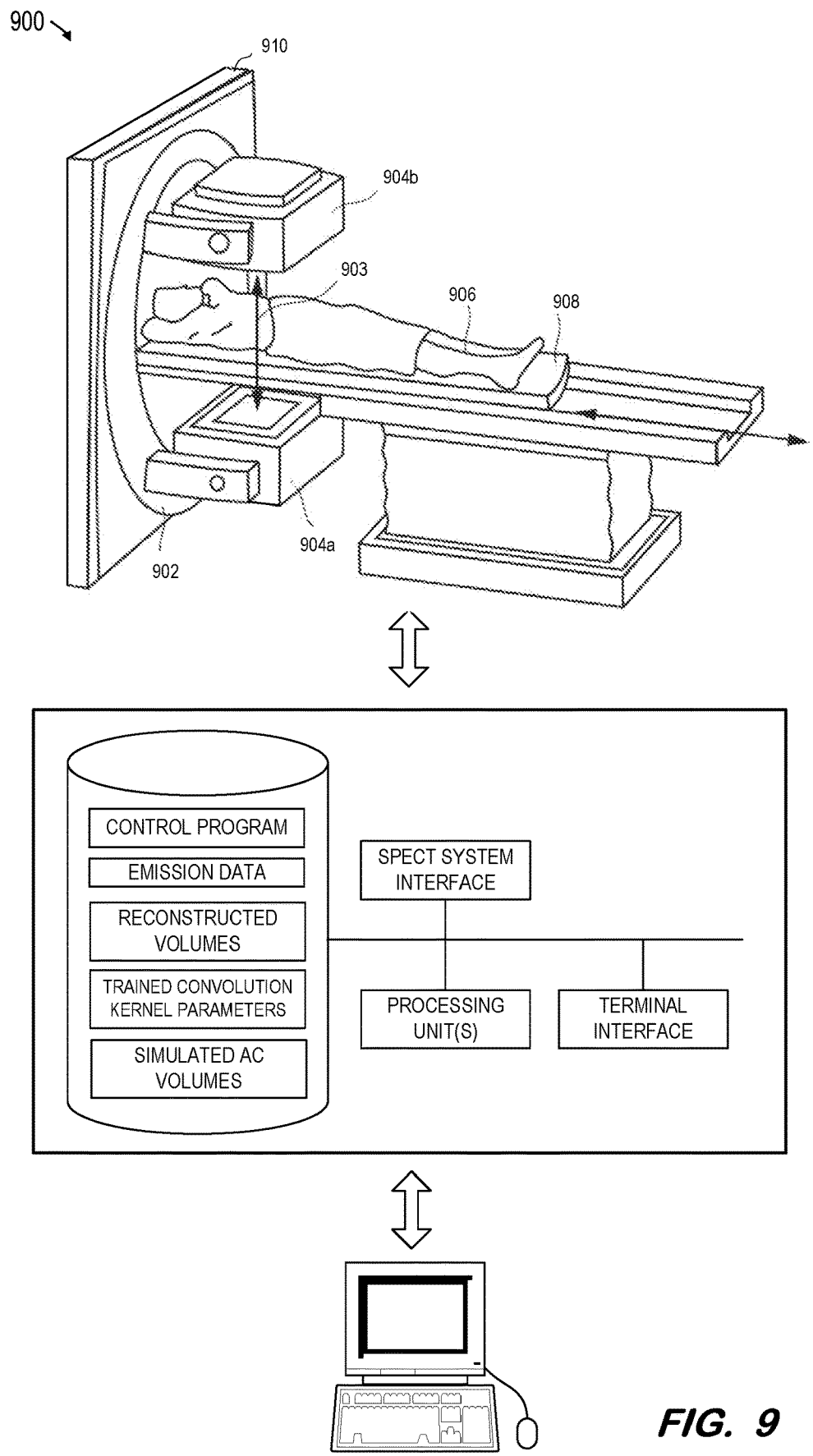
FIG. 9 illustrates an emission-only imaging system according to some embodiments.

FIG. 9 illustrates system 900 according to some embodiments. System 900 is a SPECT system which does not include a CT imaging system. System 900 may acquire pre-trained convolution kernel parameters and use the parameters to generate attenuation-corrected volumes without requiring CT data.

Embodiments are not limited to a SPECT imaging system and/or a CT imaging system as described above. For example, embodiments may employ any other imaging modalities (e.g., a magnetic resonance scanner, a positron-emission scanner, etc.) for acquiring emission data.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   a storage device;
   a processor to execute processor-executable process steps stored on the storage device to cause the system to:
      generate a plurality of non-attenuation-corrected reconstructed volumes, each of the non-attenuation-corrected reconstructed volumes generated based on a respective one of a plurality of sets of two-dimensional emission data;
      generate a plurality of attenuation-corrected reconstructed volumes, each of the attenuation-corrected reconstructed volumes generated based on a respective one of the plurality of sets of two-dimensional emission data; and
      train an artificial neural network to generate a simulated attenuation-corrected reconstructed volume from an input non-attenuation-corrected reconstructed volume, the training based on the plurality of non-attenuation-corrected volumes and respective ones of the attenuation-corrected reconstructed volumes.

2. A system according to claim 1, wherein the artificial neural network is a convolutional network, and wherein the processor is to execute processor-executable process steps to cause the system to:
   output trained kernels of the trained network to an emission imaging system.

3. A system according to claim 2, further comprising the emission imaging system, the emission imaging system to:
   acquire a set of two-dimensional emission data;
   reconstruct a non-attenuation-corrected volume based on the set of two-dimensional emission data;
   input the non-attenuation-corrected reconstructed volume to a second convolutional network comprising the trained kernels; and receive a simulated attenuation-corrected reconstructed volume generated by the second convolutional network based on the input non-attenuation-corrected reconstructed volume.

4. A system according to claim 1, further comprising an emission imaging system, the emission imaging system to:
acquire a set of two-dimensional emission data using a multi-focal non-parallel collimator;
reconstruct a non-attenuation-corrected volume based on the set of two-dimensional emission data;
input the non-attenuation-corrected reconstructed volume to the trained network; and
receive a simulated attenuation-corrected reconstructed volume generated by the trained network based on the input non-attenuation-corrected reconstructed volume.

5. A system according to claim 1, wherein the processor is to execute processor-executable process steps to cause the system to:
acquire a polar map associated with each of the non-attenuation-corrected reconstructed volumes, and wherein training the artificial neural network comprises:
training the artificial neural network to generate a simulated attenuation-corrected reconstructed volume from an input non-attenuation-corrected reconstructed volume and a polar map, the training based on the plurality of non-attenuation-corrected volumes and respective ones of the attenuation-corrected reconstructed volumes and the polar maps.

6. A system according to claim 5, wherein the processor is to execute processor-executable process steps to cause the system to:
acquire an orbit length associated with each of the non-attenuation-corrected reconstructed volumes, and wherein training the artificial neural network comprises:
training the artificial neural network to generate a simulated attenuation-corrected reconstructed volume from an input non-attenuation-corrected reconstructed volume, a polar map and an orbit length, the training based on the plurality of non-attenuation-corrected volumes and respective ones of the attenuation-corrected reconstructed volumes, the polar maps and the orbit lengths.

7. A system according to claim 1, wherein the plurality of sets of two-dimensional emission data comprise SPECT data acquired using a multi-focal non-parallel collimator.

8. A method comprising:
generating a plurality of non-attenuation-corrected reconstructed volumes, each of the non-attenuation-corrected reconstructed volumes generated based on a respective one of a plurality of sets of two-dimensional emission data;
generating a plurality of attenuation-corrected reconstructed volumes, each of the attenuation-corrected reconstructed volumes generated based on a respective one of the plurality of non-attenuation-corrected reconstructed volumes; and
training an artificial neural network to generate a simulated attenuation-corrected reconstructed volume from an input non-attenuation-corrected reconstructed volume,
the training based on the plurality of non-attenuation-corrected volumes and respective ones of the attenuation-corrected reconstructed volumes.

9. A method according to claim 8, wherein the artificial neural network is a convolutional network, and the method further comprising:
outputting trained kernels of the trained network to an emission imaging system.

10. A method according to claim 9, further comprising;
acquiring a set of two-dimensional emission data;
reconstructing a non-attenuation-corrected volume based on the set of two-dimensional emission data;
inputting the non-attenuation-corrected reconstructed volume to a second convolutional network comprising the trained kernels; and
receiving a simulated attenuation-corrected reconstructed volume generated by the second convolutional network based on the input non-attenuation-corrected reconstructed volume.

11. A method according to claim 8, further comprising:
acquiring a set of two-dimensional emission data using a multi-focal non-parallel collimator;
reconstructing a non-attenuation-corrected volume based on the set of two-dimensional emission data;
inputting the non-attenuation-corrected reconstructed volume to the trained network; and
receiving a simulated attenuation-corrected reconstructed volume generated by the trained network based on the input non-attenuation-corrected reconstructed volume.

12. A method according to claim 8, further comprising:
acquiring a polar map associated with each of the non-attenuation-corrected reconstructed volumes, and wherein training the artificial neural network comprises:
training the artificial neural network to generate a simulated attenuation-corrected reconstructed volume from an input non-attenuation-corrected reconstructed volume and a polar map, the training based on the plurality of non-attenuation-corrected volumes and respective ones of the attenuation-corrected reconstructed volumes and the polar maps.

13. A method according to claim 12, further comprising:
acquiring an orbit length associated with each of the non-attenuation-corrected reconstructed volumes, and wherein training the artificial neural network comprises:
training the artificial neural network to generate a simulated attenuation-corrected reconstructed volume from an input non-attenuation-corrected reconstructed volume, a polar map and an orbit length, the training based on the plurality of non-attenuation-corrected volumes and respective ones of the attenuation-corrected reconstructed volumes, the polar maps and the orbit lengths.

14. A method according to claim 8, wherein the plurality of sets of two-dimensional emission data comprise SPECT data acquired using a multi-focal non-parallel collimator.

15. A system comprising:
a storage device storing:
a plurality of non-attenuation-corrected reconstructed volumes, each of the plurality of non-attenuation-corrected reconstructed volumes generated based on a respective one of a plurality of sets of two-dimensional emission data;
a plurality of attenuation-corrected reconstructed volumes, each of the attenuation-corrected reconstructed volumes generated based on a respective one of the plurality of sets of two-dimensional emission data; and
nodes of an artificial neural network; and
a processor to execute processor-executable process steps stored on the storage device to cause the system to:
train the nodes of the artificial neural network to generate a simulated attenuation-corrected reconstructed volume from an input non-attenuation-corrected reconstructed volume, the training based on the plurality of non-attenuation-corrected volumes and respective ones of the plurality of attenuation-corrected reconstructed volumes.

16. A system according to claim 15, wherein the artificial neural network is a convolutional network, and wherein the processor is to execute processor-executable process steps to cause the system to:
output trained kernels of the trained network nodes to an emission imaging system.

17. A system according to claim 16, further comprising the emission imaging system, the emission imaging system to:
acquire a set of two-dimensional emission data;
reconstruct a non-attenuation-corrected volume based on the set of two-dimensional emission data;
input the non-attenuation-corrected reconstructed volume to a second convolutional network comprising the trained kernels; and
receive a simulated attenuation-corrected reconstructed volume generated by the second convolutional network based on the input non-attenuation-corrected reconstructed volume.

18. A system according to claim 15, further comprising an emission imaging system, the emission imaging system to:
acquire a set of two-dimensional emission data using a multi-focal non-parallel collimator;
reconstruct a non-attenuation-corrected volume based on the set of two-dimensional emission data;
input the non-attenuation-corrected reconstructed volume to the trained network nodes; and
receive a simulated attenuation-corrected reconstructed volume generated by the trained network nodes based on the input non-attenuation-corrected reconstructed volume.

19. A system according to claim 15, the storage device to further store a polar map associated with each of the non-attenuation-corrected reconstructed volumes, and
wherein training the nodes of the artificial neural network comprises training the nodes of the artificial neural network to generate a simulated attenuation-corrected reconstructed volume from an input non-attenuation-corrected reconstructed volume and a polar map, the training based on the plurality of non-attenuation-corrected volumes and respective ones of the attenuation-corrected reconstructed volumes and the polar maps.

20. A system according to claim 19, wherein the plurality of sets of two-dimensional emission data comprise SPECT data acquired using a multi-focal non-parallel collimator.

* * * * *